United States Patent
An et al.

(10) Patent No.: US 12,319,642 B2
(45) Date of Patent: Jun. 3, 2025

(54) METHOD OF PREPARING ACRYLONITRILE DIMER

(71) Applicant: LG CHEM, LTD., Seoul (KR)

(72) Inventors: Yu Jin An, Daejeon (KR); Wan Kyu Oh, Daejeon (KR); Ji Ha Kim, Daejeon (KR); Hyun Chul Jung, Daejeon (KR); Sae Hume Park, Daejeon (KR); Jeong Heon Ahn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 849 days.

(21) Appl. No.: 17/274,379

(22) PCT Filed: Aug. 19, 2020

(86) PCT No.: PCT/KR2020/010864
§ 371 (c)(1),
(2) Date: Mar. 8, 2021

(87) PCT Pub. No.: WO2021/118010
PCT Pub. Date: Jun. 17, 2021

(65) Prior Publication Data
US 2022/0298104 A1  Sep. 22, 2022

(30) Foreign Application Priority Data
Dec. 12, 2019 (KR) .......... 10-2019-0165340

(51) Int. Cl.
C07C 253/30  (2006.01)
B01J 31/02  (2006.01)
(Continued)

(52) U.S. Cl.
CPC ......... *C07C 253/30* (2013.01); *B01J 31/0255* (2013.01); *B01J 31/4053* (2013.01); *C07C 253/34* (2013.01)

(58) Field of Classification Search
CPC .. C07C 253/30; C07C 253/34; B01J 31/0255; B01J 31/4053
See application file for complete search history.

(56) References Cited

U.S. PATENT DOCUMENTS 3,538,141 A  11/1970 Kollar
3,732,281 A   5/1973 Feldman et al.
(Continued)

FOREIGN PATENT DOCUMENTS

CN  105837470 A  8/2016
GB    1051821 A  12/1966
(Continued)

OTHER PUBLICATIONS

McClure, J. D. "Triarylphosphine-Catalyzed Dimerization of Acrylonitrile and Related Reactions" J. Org. Chem., vol. 35, No. 9, 1970, 3045-3048. (Year: 1970).*
(Continued)

*Primary Examiner* — John S Kenyon
*Assistant Examiner* — John D McAnany
(74) *Attorney, Agent, or Firm* — BRYAN CAVE LEIGHTON PAISNER LLP

(57) ABSTRACT

Provided is a method of preparing an acrylonitrile dimer including: supplying an acrylonitrile monomer, a phosphorus-based catalyst, and an alcohol solvent to a reactor to perform a dimerization reaction to produce dimerized reactants (S10); cooling the dimerized reactants to crystallize the phosphorus-based catalyst (S20); separating the crystallized phosphorus-based catalyst (S30); and supplying the dimerized reactants from which the phosphorus-based catalyst is separated to a distillation column to separate the acrylonitrile dimer (S40).

9 Claims, 1 Drawing Sheet

(51) Int. Cl.
   *B01J 31/40*      (2006.01)
   *C07C 253/34*     (2006.01)

(56)          References Cited

U.S. PATENT DOCUMENTS

| | | | |
|---|---|---|---|
| 4,126,632 A | | 11/1978 | Hogan et al. |
| 4,316,857 A | * | 2/1982 | Gilbert ................. B01J 31/0261 |
| | | | 558/363 |
| 4,958,042 A | | 9/1990 | Shaw et al. |
| 7,482,480 B2 | * | 1/2009 | Srinivas .................. C10L 1/026 |
| | | | 554/174 |

FOREIGN PATENT DOCUMENTS

| | | |
|---|---|---|
| GB | 1546807 A | 5/1979 |
| KR | 10-1989-0005061 B1 | 12/1989 |
| KR | 10-1320413 B1 | 10/2013 |
| WO | 97/01531 A1 | 1/1997 |

OTHER PUBLICATIONS

J. D. McClure, "Triarylphosphine-Catalyzed Dimerization of Acrylonitrile and Related Reactions", J. Org. Chem., vol. 35, No. 9, 1970, pp. 3045-3048.

* cited by examiner

【Fig. 1】
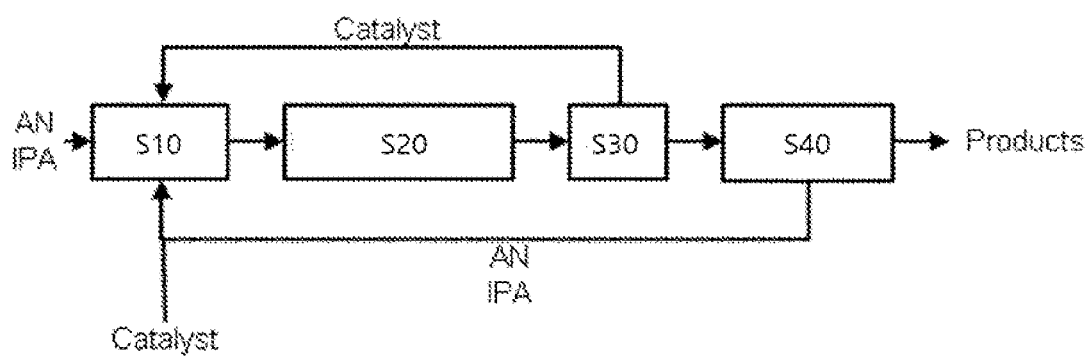
【Fig. 2】
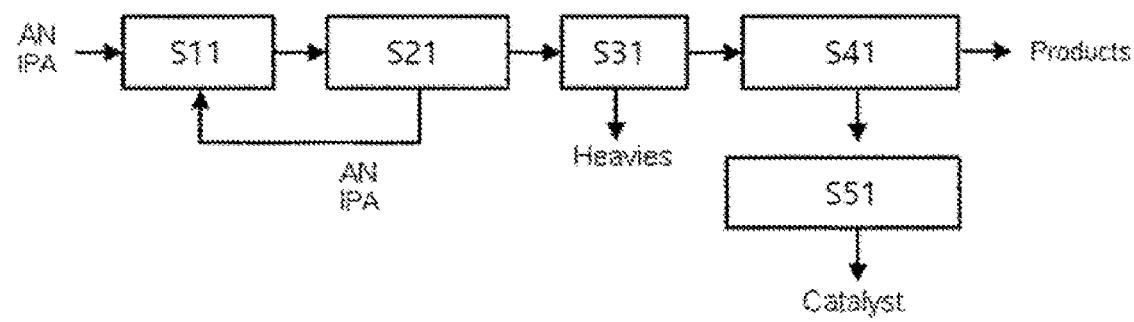

METHOD OF PREPARING ACRYLONITRILE DIMER

The present application is a National Phase entry pursuant to 35 U.S.C. § 371 of International Application No. PCT/KR2020/010864 filed on Aug. 19, 2020, and claims priority to and the benefit of Korean Patent Application No. 10-2019-0165340, filed on Dec. 12, 2019, the entire contents of which are incorporated herein by reference.

FIELD

The present invention relates to a method of preparing an acrylonitrile dimer, and more particularly, to a method of obtaining a high yield of acrylonitrile by effectively separating a phosphorus-based catalyst used as a catalyst.

BACKGROUND

An acrylonitrile dimer, in particular, a linear acrylonitrile dimer, is used as an intermediate for synthesizing hexamethylenediamine (HMDA) which is a main monomer of Nylon 66 or for the preparation of a waterproof agent, a vulcanization accelerator, and the like.

The acrylonitrile dimer may be obtained by a method of dimerizing an acrylonitrile monomer in the presence of a catalyst. Specifically, the acrylonitrile monomer may be dimerized using a ruthenium (Ru)-based compound, a cobalt (Co)-based compound, a phosphorus (P)-based compound, or the like, as a catalyst, thereby producing an acrylonitrile dimer.

A method of preparing an acrylonitrile dimer using a ruthenium-based compound among the catalysts has been mainly studied, and due to addition of hydrogen for causing a dimerization reaction, a yield of an acrylonitrile dimer and selectivity of a linear acrylonitrile dimer were lowered. That is, as hydrogen is added, hydrogenation occurs together with a dimerization reaction of acrylonitrile to produce a large amount of propionitrile, thereby lowering yield and selectivity.

Accordingly, in order to increase the yield of an acrylonitrile dimer, a method of preparing an acrylonitrile dimer using a phosphorus-based compound as a catalyst receives attention. As the method of preparing an acrylonitrile dimer using a phosphorus-based compound as a catalyst, there is a method of adding acrylonitrile to a mixed solvent including an alcohol solvent as a proton donating solvent and an inert solvent such as an aromatic hydrocarbon solvent as a reaction solvent in the presence of the phosphorus-based catalyst and performing a dimerization reaction.

However, the method had a problem in that it is difficult to separate the phosphorus-based catalyst, the acrylonitrile dimer, and the mixed solvent due to an azeotropic problem of the alcohol solvent and the aromatic hydrocarbon solvent, thereby lowering a recycling rate of the catalyst and the yield of the acrylonitrile dimer.

Specifically, separation of the phosphorus-based catalyst, the acrylonitrile dimer, and the mixed solvent has been performed by a distillation method.

The distillation method separates a catalyst by a separation method by applying heat using a characteristic of the phosphorus-based catalyst having a boiling point higher than a reactant or a product, and when the catalyst is separated from dimerized reactants by the distillation method, a continuous side reaction of acrylonitrile dimerized products proceeds by heat to produce acrylonitrile trimers, polymers, and the like, thereby lowering the yield of the acrylonitrile dimer.

Accordingly, a study of a method for simply separating a catalyst from the dimerized reactants and reusing the catalyst is currently needed.

SUMMARY

An object of the present invention is to provide a method of separating a phosphorus-based catalyst from dimerized reactants by a simple method and obtaining a high yield of an acrylonitrile dimer, in order to solve the problems mentioned in the Background.

That is, the present invention provides a method of producing an acrylonitrile dimer having a simplified catalyst separation process, by pre-separating a phosphorus-based catalyst from dimerized reactants including an acrylonitrile dimer, an unreacted acrylonitrile monomer, an alcohol solvent, and a phosphorus-based catalyst, by a recrystallization method, and separating the remaining reactants by a distillation method.

In one general aspect, a method of preparing an acrylonitrile dimer includes: supplying an acrylonitrile monomer, a phosphorus-based catalyst, and an alcohol solvent to a reactor to perform a dimerization reaction to produce dimerized reactants (S10); cooling the dimerized reactants to crystallize the phosphorus-based catalyst (S20); separating the crystallized phosphorus-based catalyst (S30); and supplying the dimerized reactants from which the phosphorus-based catalyst is separated to a distillation column to separate the acrylonitrile dimer (S40).

According to the method of preparing an acrylonitrile dimer of the present invention, a method of preparing an acrylonitrile dimer having a simplified catalyst separation process, by pre-separating a phosphorus-based catalyst from dimerized reactants including an acrylonitrile dimer, an unreacted acrylonitrile monomer, an alcohol solvent, and a phosphorus-based catalyst, by a recrystallization method, and separating the remaining reactants by a distillation method.

In addition, the phosphorus-based catalyst is separated before a distillation step, thereby preventing decomposition of the phosphorus-based catalyst due to high temperature during distillation, and a continuous side reaction of the phosphorus-based catalyst and the acrylonitrile dimer is suppressed, thereby increasing a reuse rate of the phosphorus-based catalyst and obtaining a high yield of the acrylonitrile dimer.

BRIEF DESCRIPTION OF THE DRAWINGS

FIG. 1 is a process flow chart of a method of preparing an acrylonitrile dimer according to an exemplary embodiment of the present invention.

FIG. 2 is a process flow chart of a method producing an acrylonitrile dimer according to the Comparative Example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions.

Hereinafter, the present invention will be described in more detail with reference to the following FIG. 1 for better understanding of the present invention.

According to the present invention, a method of preparing an acrylonitrile dimer is provided. The method of preparing an acrylonitrile dimer including: supplying an acrylonitrile monomer, a phosphorus-based catalyst, and an alcohol solvent to a reactor to perform a dimerization reaction to produce dimerized reactants (S10); cooling the dimerized reactants to crystallize the phosphorus-based catalyst (S20); separating the crystallized phosphorus-based catalyst (S30); and supplying the dimerized reactants from which the phosphorus-based catalyst has been separated to a distillation column to separate the acrylonitrile dimer (S40), may be provided.

According to an exemplary embodiment of the present invention, in a step for preparing the acrylonitrile dimer, raw material components, products, and the like may be transferred in the form of stream. "Stream" may refer to a fluid flow in a process, or may refer to a fluid itself flowing in a pipe. Specifically, "stream" may refer to both a fluid itself flowing in a pipe connecting each apparatus and a fluid flow. In addition, the fluid may refer to a gas or a liquid.

The acrylonitrile dimer, in particular, a linear acrylonitrile dimer, is used as an intermediate for synthesizing hexamethylenediamine (HMDA) which is a main monomer of Nylon 66, or for the preparation of a waterproof agent, a vulcanization accelerator, and the like.

Conventionally, the acrylonitrile dimer was obtained by dimerizing an acrylonitrile monomer in the presence of a catalyst and a solvent. Specifically, the acrylonitrile monomer was dimerized using a ruthenium (Ru)-based compound, a cobalt (Co)-based compound, a phosphorus (P)-based compound, or the like as a catalyst, thereby preparing an acrylonitrile dimer.

Among the catalysts used in preparing the acrylonitrile dimer, particularly, a phosphorus-based catalyst has excellent reactivity and selectivity, and the acrylonitrile dimer was prepared by a method of adding acrylonitrile to a mixed solvent including an alcohol solvent as a proton donating solvent and an inert solvent such as an aromatic hydrocarbon solvent as a reactant solvent and performing a dimerization reaction using the phosphorus-based catalyst.

However, the method had a problem that it was difficult to separate the phosphorus-based catalyst, the acrylonitrile dimer, and the mixed solvent due to an azeotropic problem of the alcohol solvent and the aromatic hydrocarbon solvent, so that a recycling rate of the catalyst and the yield of the acrylonitrile dimer were lowered.

In addition, separation of the phosphorus-based catalyst, the acrylonitrile dimer, and the mixed solvent is performed by a distillation method, and the distillation method is a method of separating a catalyst by applying heat using the characteristic of the phosphorus-based catalyst having a higher boiling point than a reactant or a product, and when the catalyst is separated from the dimerized reactant by the distillation method, the catalyst may be decomposed by heat and a side reaction of the acrylonitrile dimerized product proceeds to lower the yield of the acrylonitrile dimer due to production of an oligomer of acrylonitrile trimer, and polymer, or higher.

According to the present invention, in preparing an acrylonitrile dimer, a method of preparing an acrylonitrile dimer having a simplified catalyst separation process, by pre-separating a phosphorus-based catalyst from a dimerized reactant by a recrystallization method, and separating remaining reactants by a distillation method, is intended to be provided.

According to an exemplary embodiment of the present invention, S10 may be a step of supplying an acrylonitrile monomer, a phosphorus-based catalyst, and an alcohol solvent to a reactor 100 to perform a dimerization reaction to prepare an acrylonitrile dimer.

According to an exemplary embodiment of the present invention, in S10, the acrylonitrile dimerization reaction may be performed by a common method known in the art. For example, an appropriate amount of a raw material is supplied to the reactor and the acrylonitrile dimerization reaction may be performed in optimal temperature range and pressure range.

For example, the acrylonitrile dimerization reaction may be performed in a temperature range of 0° C. to 100° C., 10° C. to 80° C., or 40° C. to 80° C., and in a pressure range of 1 bar to 5 bar, 1 bar to 4 bar, or 1 bar to 3 bar. When the acrylonitrile dimerization reaction is performed in the above temperature range and pressure range, the acrylonitrile dimer may be prepared with an excellent conversion rate.

According to an exemplary embodiment of the present invention, the phosphorus-based catalyst may be represented by the following Chemical Formula 1:

[Chemical Formula 1]

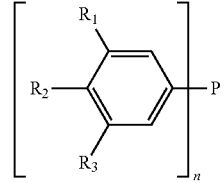

wherein $R_1$ to $R_3$ are, independently from one another, hydrogen, an alkyl group having 1 to 5 carbon atoms, an amino group, or an alkoxy group, and n is an integer of 1 to 3.

As a specific example, the phosphorus-based catalyst may be a compound of Chemical Formula 1 wherein $R_1$ to $R_3$ are, independently from one another, hydrogen or an alkyl group having 1 to 3 carbon atoms, and n is 3. As a more specific example, the phosphorus-based catalyst may be a compound of Chemical Formula 1 wherein $R_1$ to $R_3$ are independently of one another hydrogen and n is 3.

The phosphorus-based catalyst may be solid at room temperature. Specifically, the phosphorus-based catalyst may be present in a solid state at room temperature and present in a liquid state dissolved in a reactant solvent at reaction temperature for acrylonitrile dimerization. Through the characteristic as such, the phosphorus-based catalyst may be easily separated from the dimerized reactants by recrystallization and separation in S20 and S30.

According to an exemplary embodiment of the present invention, the alcohol solvent may include for example, one or more selected from the group consisting of methanol, ethanol, isopropyl alcohol, and cyclohexyl alcohol. As a specific example, the alcohol solvent may be ethanol or isopropyl alcohol.

The phosphorus-based catalyst may have a low solubility in the alcohol solvent. Specifically, in the alcohol solvent, only the phosphorus-based catalyst has a selectively low solubility, and thus, the alcohol solvent may be useful in recrystallizing and separating the phosphorus-based catalyst in S20 and S30 described later. In addition, the phosphorus-based catalyst has a low solubility in the alcohol solvent, and also the alcohol solvent is suitable as an acrylonitrile dimerization reaction solvent and may be used as a proton donor.

According to an exemplary embodiment of the present invention, the alcohol solvent may be used alone as the reaction solvent in S10. Specifically, an alcohol solvent in which the phosphorus-based catalyst has a low solubility, and which is suitable as the acrylonitrile dimerization reaction solvent and may be used as a proton donor, may be used alone in S10. In this case, as compared with a reaction solvent used in the conventional acrylonitrile dimerization reaction in which the alcohol solvent and the aromatic hydrocarbon solvent are used in combination, the phosphorus-based catalyst may be easily recovered and the reuse rate of the catalyst may be improved. In addition, since the aromatic hydrocarbon solvent is not used, it may be easy to separate the acrylonitrile dimer by subsequent distillation.

According to an exemplary embodiment of the present invention, in S10, the dimerized reactants may be produced by the acrylonitrile dimerization reaction. Specifically, the dimerized reactants may include the acrylonitrile dimer, an unreacted acrylonitrile monomer, the alcohol solvent, and the phosphorus-based catalyst.

According to an exemplary embodiment of the present invention, S20 may be a step for separating the phosphorus-based catalyst in the dimerized reactants produced by the acrylonitrile dimerization reaction in S10. Specifically, the dimerized reactants in which the acrylonitrile dimer, the unreacted acrylonitrile monomer, the alcohol solvent, and the phosphorus-based catalyst are mixed are cooled to crystallize the phosphorus-based catalyst in the reactants.

According to an exemplary embodiment of the present invention, the temperature of the dimerized reactants in S20 may be cooled to −50° C. to 0° C. For example, the temperature of the dimerized reactant in S20 may be cooled to a range of −40° C. to 0° C., −30° C. to 0° C., or −20° C. to −5° C. By cooling the dimerized reactants to the range, the phosphorus-based catalyst in the dimerized reactants may be selectively crystallized to be precipitated as a solid.

S20 may be performed in the reactor or may be performed in a separate device after supplying the dimerized reactants to the separate device for crystallization such as a batch crystallizer.

According to an exemplary embodiment of the present invention, S30 may be a step for separating the phosphorus-based catalyst precipitated by cooling the dimerized reactants in S20 from other reactants.

Specifically, since the phosphorus-based catalyst is selectively crystallized and precipitated as a solid in S20, it may be easy to separate the phosphorus-based catalyst in S30. Specifically, the phosphorus-based catalyst may be separated by a simple method using a filter in S30. For example, the filter may be a filtration net, and the filtration net may have a mesh size to pass the unreacted acrylonitrile, the acrylonitrile dimer, and the alcohol solvent which are in a liquid state, and to filter the phosphorus-based catalyst precipitated in a solid state. Thus, the phosphorus-based catalyst used in the acrylonitrile dimerization reaction may be simply separated at low cost and reused.

The phosphorus-based catalyst precipitated in a solid state, separated in S30 may be reused by resupplying the catalyst for the acrylonitrile dimerization reaction in S10.

According to an exemplary embodiment of the present invention, S40 may be a step for separating the acrylonitrile dimer which is the product of the acrylonitrile dimerization reaction from the dimerized reactants remaining after separating the phosphorus-based catalyst, that is, the unreacted acrylonitrile monomer, the acrylonitrile dimer, and the alcohol solvent.

Specifically, in S40, the dimerized reactants from which the phosphorus-based catalyst is separated in S30 may be supplied to the distillation column to separate the unreacted acrylonitrile monomer and the alcohol solvent from an upper portion of the distillation column and to separate the acrylonitrile dimer from a lower portion of the distillation column.

An operation temperature of the distillation column may be 60° C. to 110° C. For example, the operation temperature of the distillation column may be 70° C. to 110° C., 70° C. to 100° C., or 70° C. to 90° C. In addition, an operation pressure of the distillation column may be 0.001 bar to 3 bar. For example, the operation pressure of the distillation column may be 0.001 bar to 2 bar, 0.01 bar to bar, or 0.01 bar to 1.5 bar. By controlling the operation temperature and operation pressure of the distillation column to the above ranges, the acrylonitrile dimer is not distilled and the unreacted acrylonitrile monomer and the alcohol solvent are distilled from the upper portion of the distillation column, and thus, the unreacted acrylonitrile monomer and the alcohol solvent may be separated from the upper portion of the distillation column and the acrylonitrile dimer may be effectively separated from the lower portion of the distillation column.

In S40, the unreacted acrylonitrile monomer and the alcohol solvent separated from the upper portion of the distillation column may be supplied to the reactor and reused in the acrylonitrile dimerization reaction.

In S40, the acrylonitrile dimer separated from the lower portion of the distillation column may include a linear acrylonitrile dimer including one or more selected from the group consisting of 1,4-dicyanobutene and 2-methyleneglutaronitrile.

In S40, the yield of the acrylonitrile dimer separated from the lower portion of the distillation column may be 80% or more, 80% to 95%, or 85% to 95%. In addition, in S40, a ratio of 1,4-dicyanobutene and 2-methyleneglutaronitrile of the acrylonitrile dimer separated from the lower portion of the distillation column may be 1:1 to 1:5, 1:1.5 to 1.4, or 1:2 to 1:4.

As such, the phosphorus-based catalyst in the dimerized reactants is separated first through S30, the dimerized reactants from which the phosphorus-based catalyst is separated are supplied to the distillation column to separate and obtain the acrylonitrile dimer, thereby improving the yield of the acrylonitrile dimer and the selectivity of the acrylonitrile dimer.

According to an exemplary embodiment of the present invention, in the method of preparing an acrylonitrile dimer, a distillation column, a condenser, a reboiler, a pump, a compressor, a mixer, a separator, and the like may be further installed, if necessary.

Hereinabove, the method of preparing an acrylonitrile dimer according to the present invention has been described and illustrated in the drawings; however, the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the method of preparing an acrylonitrile dimer according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

As shown in the process flow chart illustrated in FIG. 1, 3 mL of an acrylonitrile monomer (AN), 10 mL of isopropyl alcohol (IPA), and 5 mol % of a phosphorus-based catalyst represented by the following Chemical Formula 2 (Sigma-Aldrich, triphenylphosphine) relative to an acrylonitrile monomer were supplied to a reactor, and an acrylonitrile dimerization reaction was performed at a temperature of 60° C. under a ambient pressure to obtain dimerized reactants (S10).

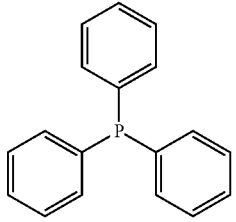

[Chemical Formula 2]

Then, the dimerized reactants were cooled to −38° C. in the reactor to precipitate the phosphorus-based catalyst as a solid (S20).

Next, the phosphorus-based catalyst precipitated as a solid in the dimerized reactants was filtered using a filter (S30).

Next, the dimerized reactants from which the phosphorus-based catalyst was separated were supplied to a distillation column, a temperature of the distillation column was controlled to 100° C. and a pressure thereof was controlled to 0.08 bar to separate an unreacted acrylonitrile monomer and isopropyl alcohol from an upper portion of the distillation column and supply them to the reactor, and an acrylonitrile dimer (product) was obtained from a lower portion of the distillation column (S40).

COMPARATIVE EXAMPLE

Comparative Example 1

As shown in the process flow chart illustrated in FIG. 2, 3 mL of an acrylonitrile monomer, 10 mL of isopropyl alcohol, and 5 mol % of a phosphorus-based catalyst represented by the following Chemical Formula 2 (Sigma-Aldrich, triphenylphosphine) relative to an acrylonitrile monomer were supplied to a reactor, and an acrylonitrile dimerization reaction was performed in a temperature of 60° C. under a ambient pressure to obtain dimerized reactants (S11).

Then, the dimerized reactants were supplied to a first distillation column, a temperature of the first distillation column was controlled to 100° C. and a pressure thereof was controlled to 0.08 bar to separate the unreacted acrylonitrile monomer and isopropyl alcohol from an upper portion of the first distillation column and supply them to the reactor, and the remaining material was separated from a lower portion of the first distillation column (S21).

Next, in addition to the acrylonitrile dimer and the phosphorus-based catalyst in the components separated from the lower portion of the first distillation column, heavy components produced from a continuous side reaction of the acrylonitrile dimer and the phosphorus-based catalyst were removed using a filter (S31).

Next, the acrylonitrile dimer and the phosphorus-based catalyst were supplied to a second distillation column, a temperature of the second distillation column was controlled to 120 ° C. and a pressure thereof was controlled to 3.9 mbar to separate and obtain the acrylonitrile dimer from an upper portion of the second distillation column, and the phosphorus-based catalyst was separated from a lower portion of the second distillation column (S41).

Next, the phosphorus-based catalyst separated from the lower portion of the second distillation column was supplied to a batch crystallizer, and isopropyl alcohol was further supplied as a solvent to the batch crystallizer, and the phosphorus-based catalyst was dissolved in isopropyl alcohol while the temperature was increased to 70° C. Next, the temperature was cooled to −38° C. to crystallize the phosphorus-based catalyst to be precipitated as a solid, and then recover the catalyst (S51).

Upon review of Example 1 and Comparative Example 1, in Example 1, the dimerized reactants were cooled to separate the phosphorus-based catalyst first, the unreacted acrylonitrile monomer and isopropyl alcohol were separated from the upper portion of the distillation column and supplied to the reactor, and the acrylonitrile dimer was separated from the lower portion of the distillation column, thereby simplifying the process.

Upon comparison, in Comparative Example 1 which is the conventional technology, the dimerized reactants were supplied to the first distillation column to separate the unreacted acrylonitrile monomer and isopropyl alcohol from the upper portion and to separate the residue from the lower portion. Here, since the first distillation column was operated at an acrylonitrile dimerization reaction temperature or higher, heavy components were produced by the continuous reaction of the acrylonitrile dimer and the phosphorus-based catalyst in the lower portion of the first distillation column. Therefore, in Example 1, a filtering step (S31) was required for removing the heavy components which are not needed.

In addition, since in Comparative Example 1, the phosphorus-based catalyst was not separated first from the dimerized reactants, two or more distillation columns were required. Specifically, the first distillation column for separating unreacted acrylonitrile and isopropyl alcohol from the dimerized reactants and the second distillation column for separating the acrylonitrile dimer and the phosphorus-based catalyst were required. Thus, Comparative Example 1 had a problem of having a complicated process and increased costs associated with additional equipment as compared with Example 1.

In addition, Comparative Example 1 requires a separate solvent additionally for recrystallizing the phosphorus-based catalyst separated from the lower portion of the second distillation column. In addition, Comparative Example 1 further requires a step of heating for dissolving the separated phosphorus-based catalyst and the solvent. Thus, Comparative Example 1 had a problem of having additional costs of the solvent and increased energy use amount as compared with Example 1.

The invention claimed is:

1. A method of preparing an acrylonitrile dimer, the method comprising:
supplying an acrylonitrile monomer, a phosphorus-based catalyst, and a solvent to a reactor to perform a dimerization reaction to produce dimerization reaction products, wherein the solvent comprises an alcohol and does not contain an aromatic hydrocarbon solvent;
cooling the reaction products to crystallize the phosphorus-based catalyst;
separating the crystallized phosphorus-based catalyst from the reaction products containing an unreacted acrylonitrile monomer, the acrylonitrile dimer, and the solvent; and
supplying the reaction products from which the phosphorus-based catalyst is separated to a distillation column to separate the acrylonitrile dimer,
wherein in separating the acrylonitrile dimer, the reaction products from which the phosphorus-based catalyst is separated are supplied to the distillation column, a first fraction containing the unreacted acrylonitrile monomer and the solvent are separated to an upper portion of the distillation column from which it is collected, and a second fraction containing the acrylonitrile dimer is separated to a lower portion of the distillation column from which it is collected, and
wherein cooling the reaction products and separating of the crystallized phosphorus- based catalyst are performed prior to separating any of the unreacted acrylonitrile monomer. the solvent, or the acrylonitrile dimer contained in the reaction products.

2. The method of preparing an acrylonitrile dimer of claim 1, wherein the phosphorus-based catalyst is represented by the following Chemical Formula 1:

[Chemical Formula 1]

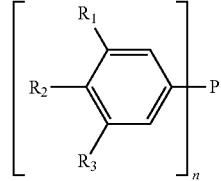

wherein
$R_1$ to $R_3$ are, independently from one another, hydrogen, an alkyl group having 1 to 5 carbon atoms, an amino group, or an alkoxy group, and
n is an integer of 1 to 3.

3. The method of preparing an acrylonitrile dimer of claim 2, wherein in Chemical Formula 1, $R_1$ to $R_3$ are, independently from one another, hydrogen or an alkyl group having 1 to 3 carbon atoms, and n is 3.

4. The method of preparing an acrylonitrile dimer of claim 1, wherein the alcohol comprises one or more of methanol, ethanol, isopropyl alcohol, and cyclohexyl alcohol.

5. The method of preparing an acrylonitrile dimer of claim 4, wherein the solvent is ethanol or isopropyl alcohol.

6. The method of preparing an acrylonitrile dimer of claim 1, wherein in cooling the reaction products to crystallize the phosphorus-based catalyst, the reaction products are cooled to −50° C. to 0° C.

7. The method of preparing an acrylonitrile dimer of claim 1, wherein the crystallized phosphorus-based catalyst is separated using a filter.

8. The method of preparing an acrylonitrile dimer of claim 1, wherein the separated phosphorus-based catalyst is reused in the dimerization reaction.

9. The method of preparing an acrylonitrile dimer of claim 1, wherein the separated unreacted acrylonitrile monomer and the alcohol solvent are reused in the dimerization reaction.

* * * * *